United States Patent
Mao et al.

(10) Patent No.: US 6,626,836 B2
(45) Date of Patent: Sep. 30, 2003

(54) ADAPTIVE SIGNAL PROCESSING SCHEME FOR CONTRAST AGENT IMAGING

(75) Inventors: Zuhua Mao, Issaquash, WA (US); Hui Jiang, Issaquash, WA (US); Patrick L. Von Behren, Bellevue, WA (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 09/825,814

(22) Filed: Apr. 4, 2001

(65) Prior Publication Data
US 2002/0147399 A1 Oct. 10, 2002

(51) Int. Cl.7 ............................................. A61B 8/00
(52) U.S. Cl. ...................................... 600/455; 600/458
(58) Field of Search ................................. 600/443, 447, 600/454, 450, 455, 453, 458

(56) References Cited

U.S. PATENT DOCUMENTS

| | | | |
|---|---|---|---|
| 5,494,037 A | 2/1996 | Banjanin et al. | 128/661.09 |
| 5,632,277 A | 5/1997 | Chapman et al. | 128/660.07 |
| 5,706,819 A | 1/1998 | Hwang et al. | 128/662.02 |
| 5,897,500 A | 4/1999 | Zhao | 600/443 |
| 5,961,464 A * | 10/1999 | Poland | 600/458 |
| 5,980,459 A * | 11/1999 | Chiao et al. | 600/447 |
| 6,050,946 A * | 4/2000 | Teo | 600/443 |
| 6,095,980 A * | 8/2000 | Burns et al. | 600/453 |
| 6,102,858 A | 8/2000 | Hatfield et al. | 600/443 |
| 6,131,458 A | 10/2000 | Langdon et al. | 73/627 |
| 6,132,377 A * | 10/2000 | Bolorforosh et al. | 600/458 |
| 6,181,810 B1 * | 1/2001 | Zhang et al. | 382/128 |
| 6,186,950 B1 * | 2/2001 | Averkiou et al. | 600/440 |
| 6,190,322 B1 * | 2/2001 | Clark | 600/443 |
| 6,213,947 B1 * | 4/2001 | Phillips | 600/443 |
| 6,213,951 B1 * | 4/2001 | Krishnan et al. | 600/458 |

* cited by examiner

Primary Examiner—Marvin M. Lateef
Assistant Examiner—Maulin M Patel

(57) ABSTRACT

An ultrasound system includes a transmit/receive switch (502), at least one frequency band selection circuit (512), and a selection unit (511). The selection unit (511) is used to determine if the data being received are from tissue or contrast agent regions. Depending on which type of region the data are from, different signal processing techniques are applied to the data. For example for tissue regions, a harmonic filter can be applied to the signal. If the signals are from contrast agent flow regions, both the harmonic filter and a fundamental filter can be used.

22 Claims, 8 Drawing Sheets

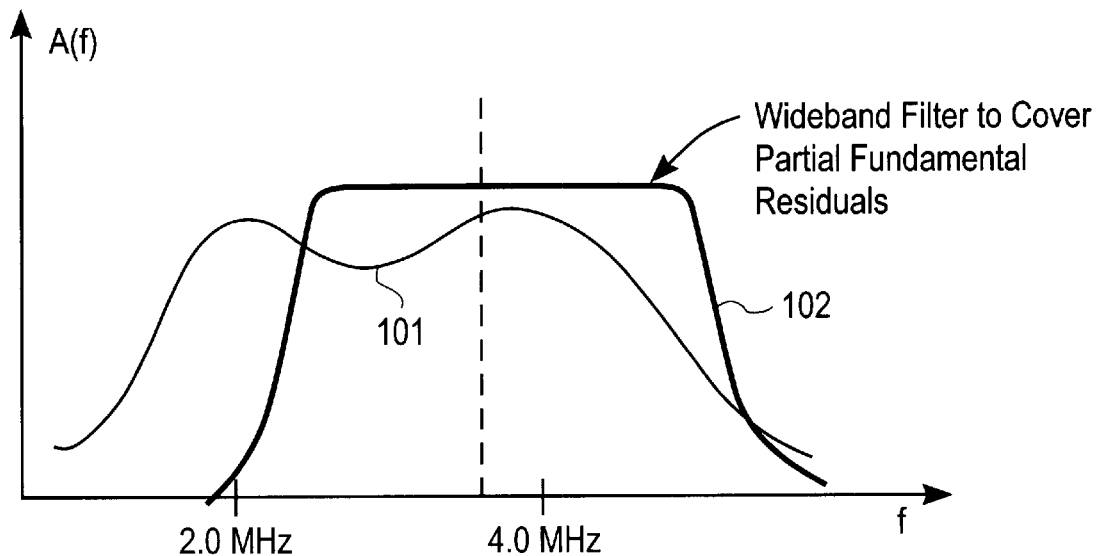
FIG. 1  Spectrum of Contrast Agent Flow Using PI Wideband Harmonic Scheme.
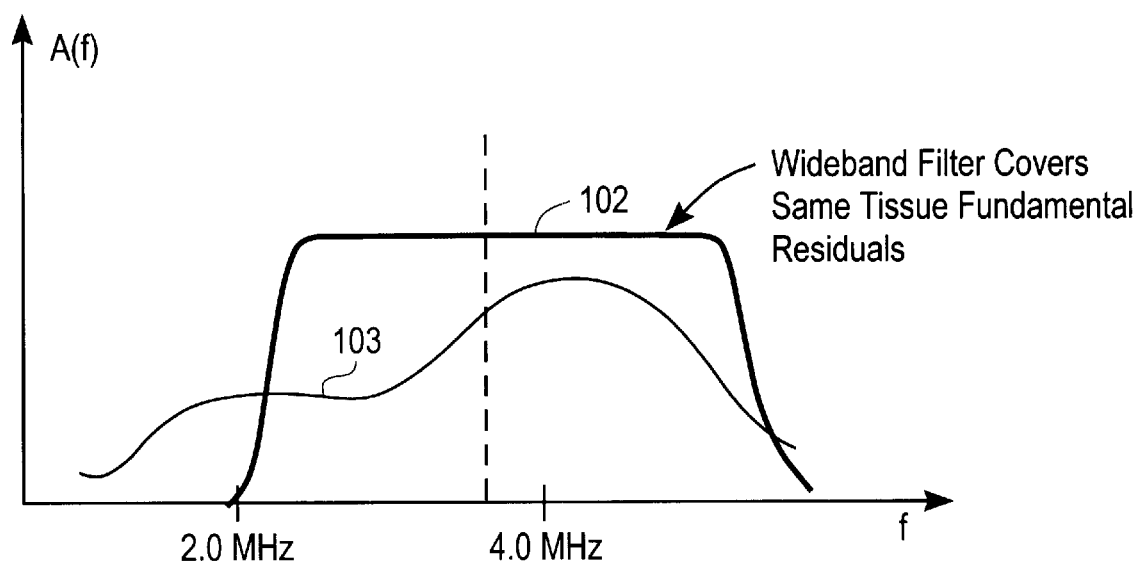
FIG. 2  Tissue Spectrum With PI Wideband Harmonic Imaging Scheme.

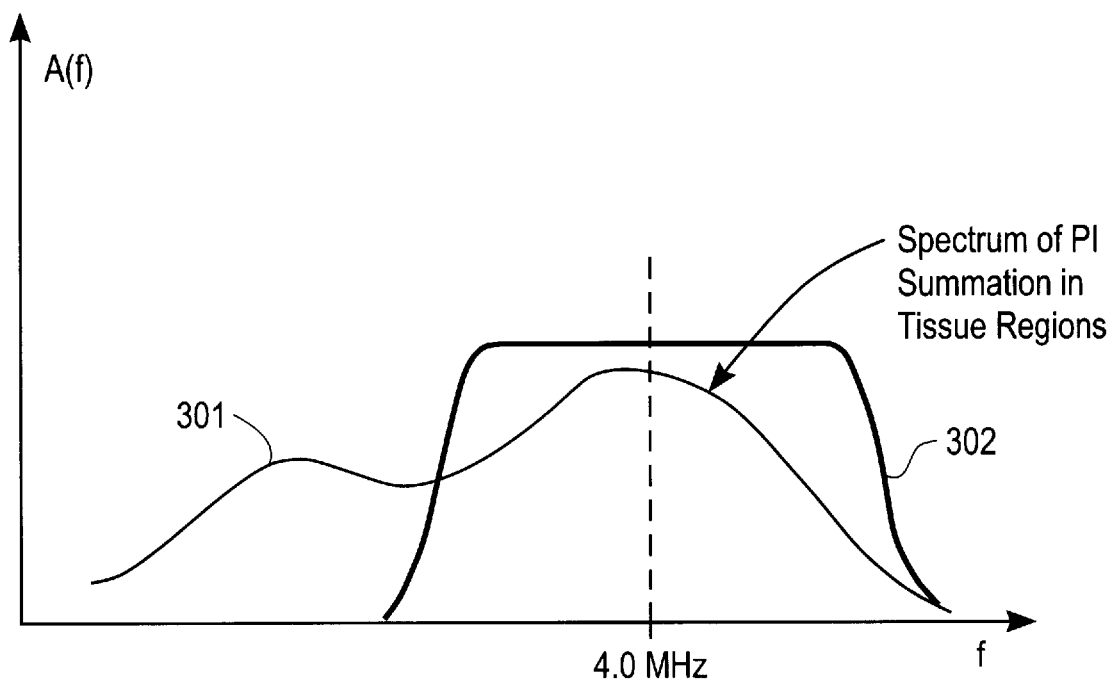
FIG. 3  A Harmonic Filter is Used for Tissue Regions.
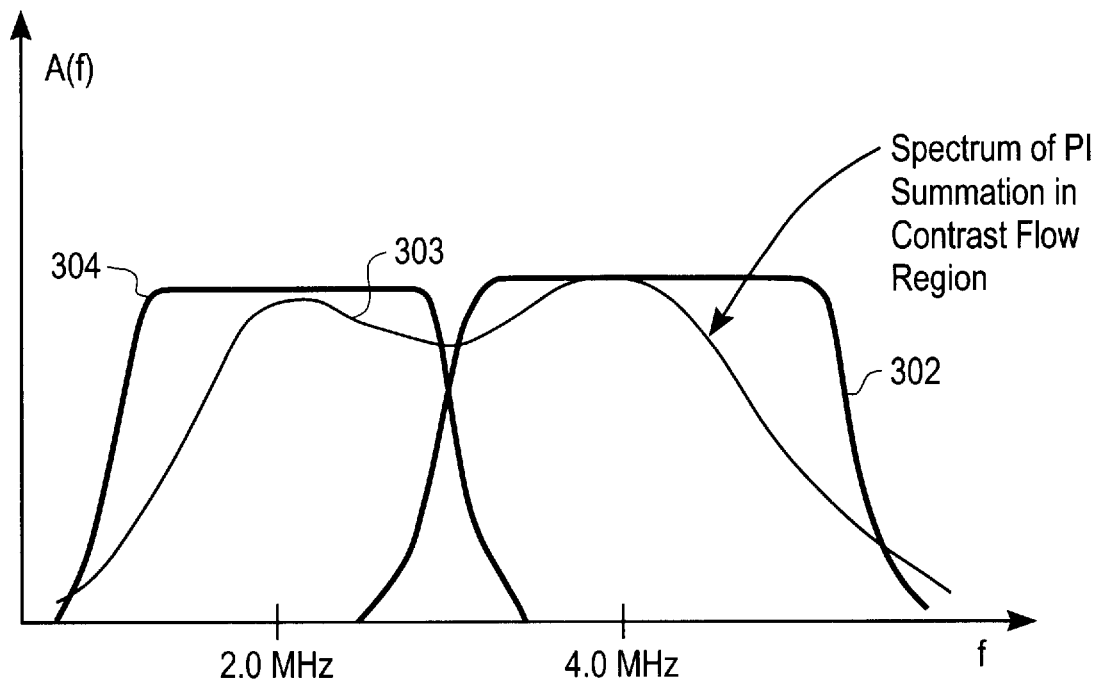
FIG. 4  Two Filters Are Used For Compounding of Contrast Agent Flow. The Harmonic Filter is the Same as for Tissue Region. Another Filter is Used to Detect PI Fundamental Residuals.

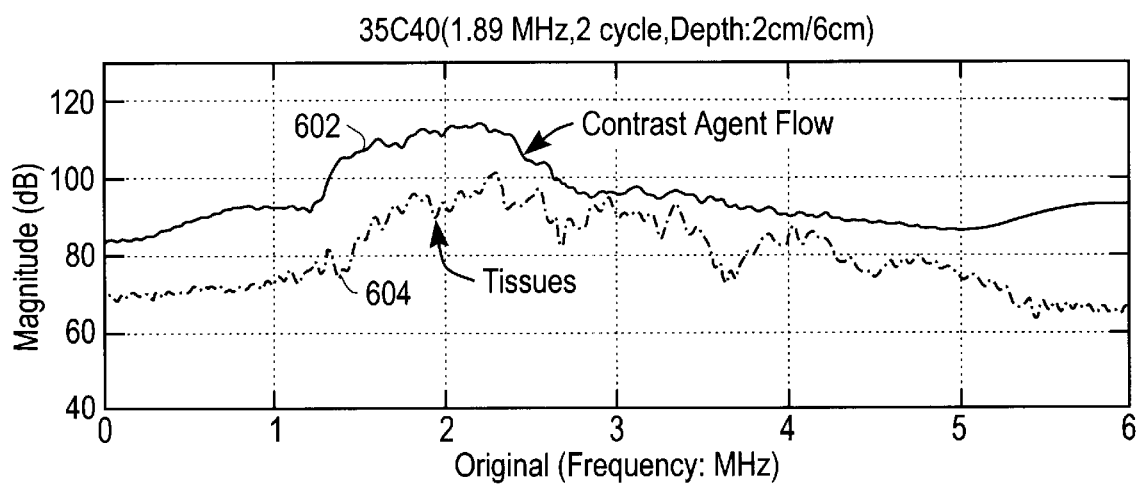
FIG. 6  The Spectra of Echoes from Single Transmit.
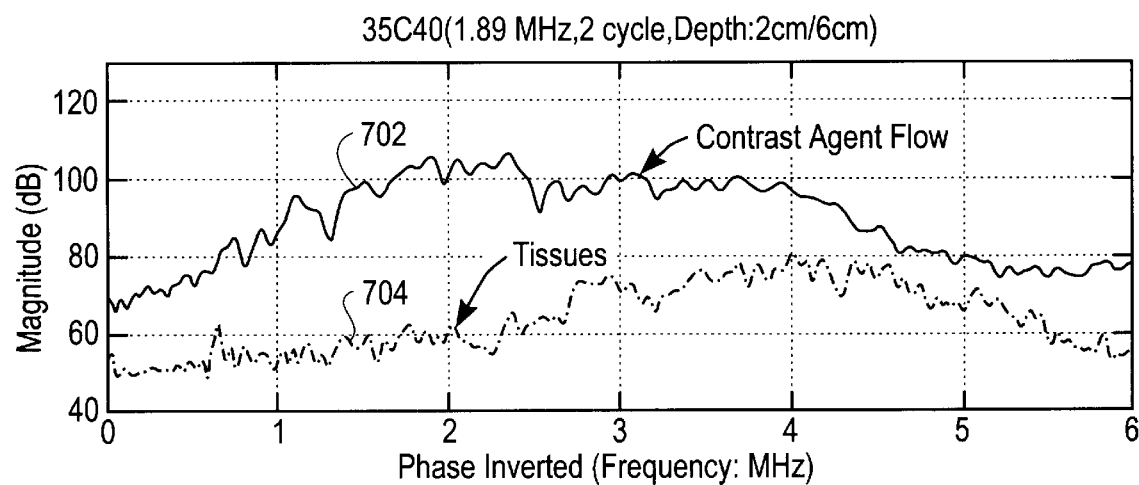
FIG. 7  The Spectrum of Echoes with PI Summation

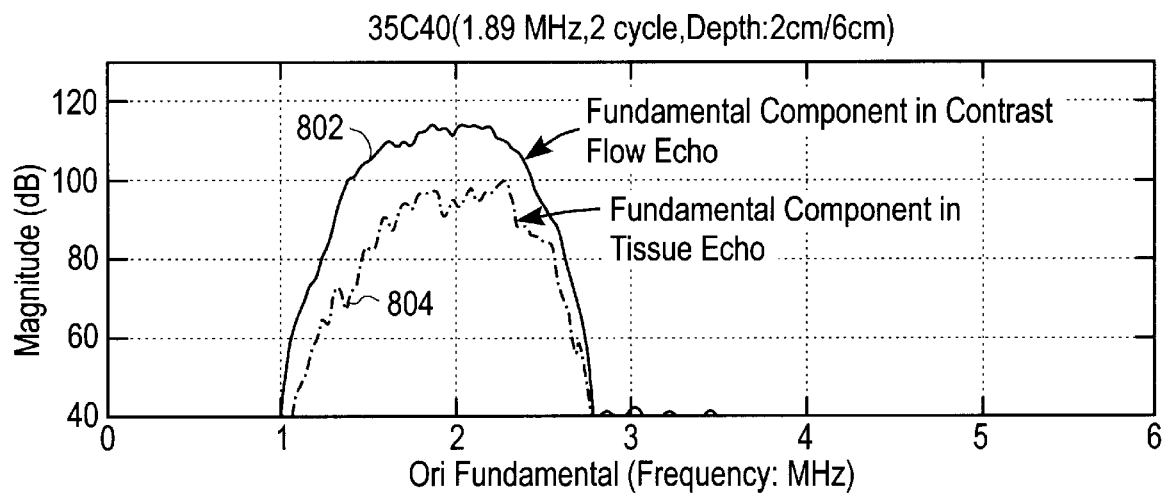
FIG. 8  The Spectra of Fundamental Components Using a Filter with Lo at 2.0 MHz for Single Transmit.
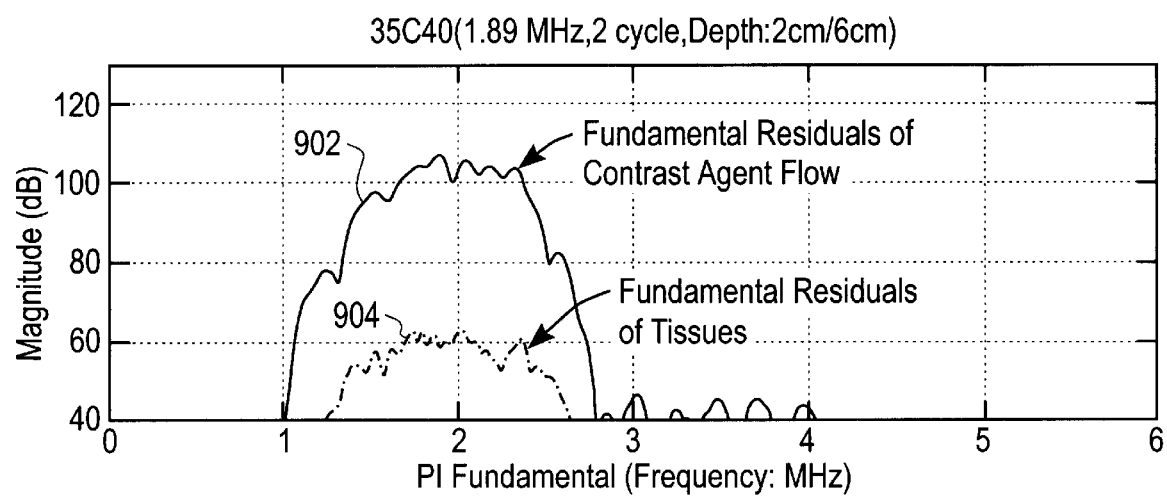
FIG. 9  The Spectra of Fundamental Residuals Using a Filter with Lo at 2.0 MHz for PI Summation Signals.

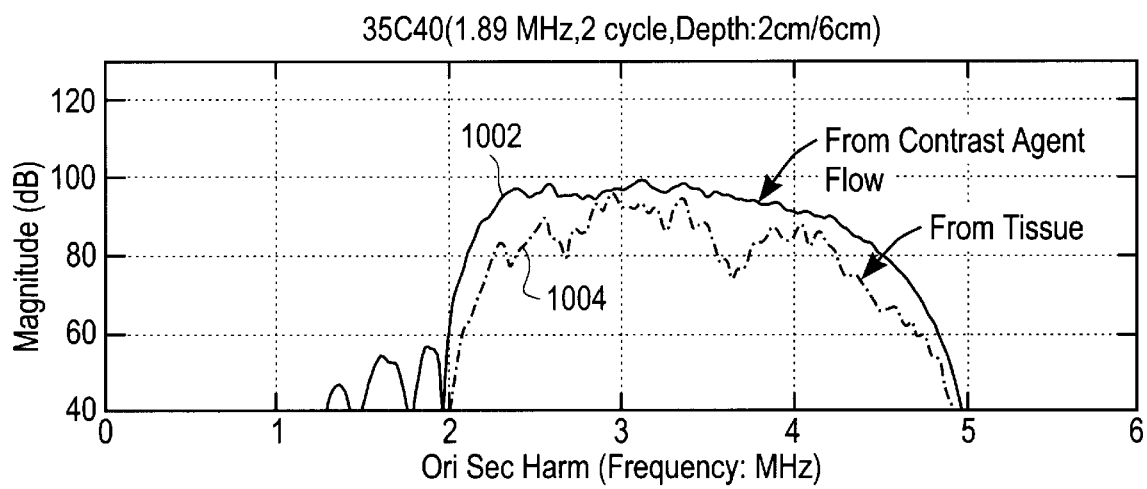
FIG. 10 The 2nd Harmonic Components of Single Transmit Passing a Harmonic Filter with Lo = 4.0 MHz
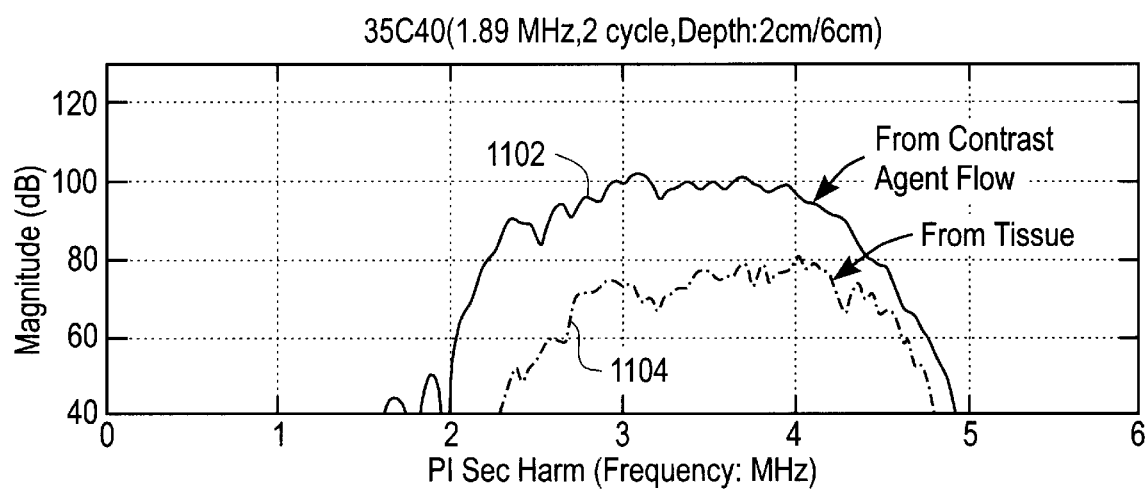
FIG. 11 The 2nd Harmonic Components of PI Summation Passing a 2nd Harmonic Filter with Lo = 4.0 MHz

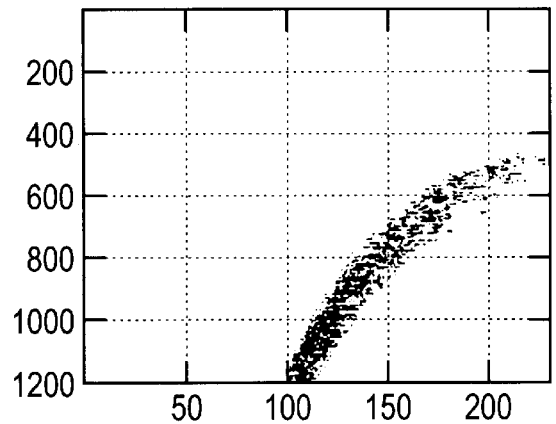
FIG. 12  Adaptive Frequency Compounding Result
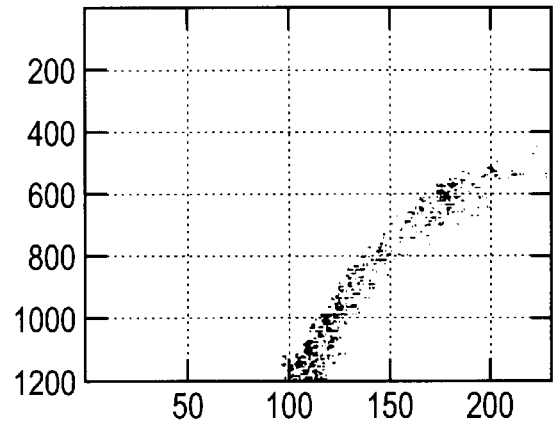
FIG. 13  Second Harmonic Only Image
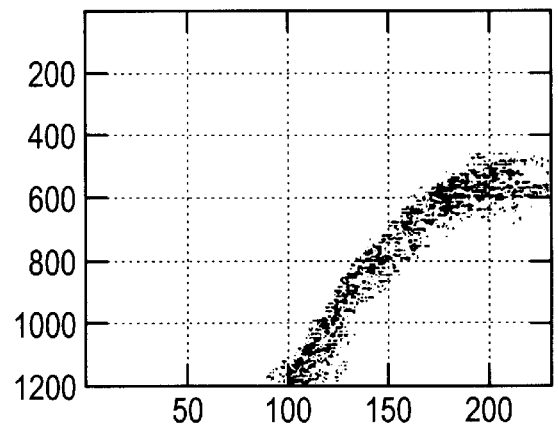
FIG. 14  Wideband Harmonic Imaging Result

ADAPTIVE SIGNAL PROCESSING SCHEME FOR CONTRAST AGENT IMAGING

BACKGROUND OF THE INVENTION

FIELD OF THE INVENTION

The present invention relates to ultrasound systems and, in particular, an improved system and method for contrast agent imaging.

DESCRIPTION OF THE RELATED ART

In ultrasound imaging, ultrasonic waves are transmitted into a body from the surface of the skin and are reflected from tissues and cells within the body. The reflected echoes are received by an ultrasonic transducer and processed to produce an image or measurement of blood flow.

Materials known as "ultrasonic contrast agents" can be introduced into the body to enhance ultrasonic diagnosis. Contrast agents are substances which will strongly interact with ultrasonic waves, returning echoes which may be clearly distinguished from those returned by blood or tissue. One class of substances which has been found to be useful in an ultrasonic contrast agent is gas, in the form of microbubbles. Microbubbles present a significant acoustic impedance mismatch in comparison to tissue and fluids and nonlinear behavior in certain acoustic fields which is readily detectable through special ultrasonic processing.

Certain microbubble contrast agents exhibit significant detectable nonlinear responses at frequencies other than the transmitted ultrasound frequency. This property is useful for clutter rejection of the received signals. When the transmitted frequency band is used as the receive frequency band, echoes will be returned from the microbubbles, but also from the surrounding tissue, the latter as clutter in the received echo signals. But with contrast agents, significant return energy is concentrated outside the fundamental transmit frequency band, so that fundamental band clutter from tissue can be ignored. Since tissue generally reflects relatively minimal energy outside the fundamental band, the received energy outside the fundamental band enables the microbubble echoes to be received with a high signal to noise ratio.

A useful technique for contrast enhancement is known as phase inversion. According to one implementation of this technique, first and second ultrasound pulses are alternatively transmitted into the specimen being imaged. The pulses are amplitude modulated signals; the first pulse differs from the second by the phase, for example, by 180 degrees. The echo signals generated are measured and combined. Echoes generated by linear media cancel, but will not cancel if an echo results from a nonlinear medium. Further details regarding this technique are described in commonly-assigned U.S. Pat. No. 5,632,277, titled "Ultrasonic Imaging System Employing Phase Inversion Subtraction to Enhance the Image."

The wideband phase inversion scheme receives harmonic signals along with fundamental residuals, flow motion, and non-symmetrical bubble responses to compression and rarefaction pulses.

This technique is illustrated in greater detail in FIGS. 1 and 2. More particularly, FIG. 1 is a graph illustrating the spectrum 101 of contrast agent flow using phase inversion wideband imaging. A wideband receiving filter 102 is positioned at 2.0 MHz to 6 MHz, where 2.0 MHz is the first harmonic. It is noted that these frequency values are exemplary only. As can be seen, a substantial portion of the contrast agent flow spectrum falls within the wideband filter, i.e., the second harmonic and partial fundamental residuals.

FIG. 2 illustrates the corresponding tissue spectrum 103, with the same wideband filter 102. It is known that the phase inversion imaging scheme achieves 25–30 dB fundamental cancellations in tissue regions. As a result, tissue second harmonic signals are stronger than fundamental residuals. Thus, in tissue regions, the spectra of phase inversion summation signals exhibit double humps within the band of the wideband filter. As such, while the wideband filter is beneficial to contrast flow enhancement, it degrades both image spatial resolution and contrast resolution in tissue regions.

As such, there is a need for a system having improved image quality in tissue regions and enhanced flow sensitivity in flow regions.

SUMMARY OF THE INVENTION

These and other problems in the prior art are overcome in large part by a system and method according to the present invention. An ultrasound system according to the present invention employs analysis of multiple frequency bands to distinguish between tissue and contrast agents. Since tissue is primarily a linear scatterer, with relatively minimal energy outside of the fundamental band and contrast agents significantly scatter more energy outside of the fundamental band, a selection unit can distinguish between tissue regions and contrast regions and apply different processing to each region.

In one embodiment, the selection unit employs the parameter B/A to distinguish between tissue and contrast agent signals.

In another embodiment, an ultrasound system according to the present invention employs a harmonic imaging filter on tissue only regions and implements frequency compounding filtering for contrast agent flow regions.

In another embodiment, tissue regions are displayed using grayscale maps and contrast agent regions are displayed in color.

In another embodiment, tissue regions are processed using echo processing techniques and displayed using grayscale maps while contrast agent regions are processed using power doppler and displayed using power doppler maps.

An ultrasound system according to the present invention can include a transmit/receive switch, an amplifier, analog-to-digital converters an RF data memory, frequency band selection means for selecting at least two frequency bands, and a region type selection unit. The region type selection unit can be used to determine if the data being received are from tissue or contrast agent regions. The frequency band selection means can be a first filter downconverter and second filter downconverter, one of which may be centered at a harmonic frequency while the other may be centered at the fundamental frequency. If the received signals are from tissue regions, a harmonic filter can be applied to the signal. If the signals are from contrast agent flow regions, both the harmonic filter and a fundamental filter can be used.

One method of generating 2 receive bands is a 2 pulse phase inversion method. This method includes generating and receiving two transmit pulses. The first pulse differs from the second by approximately 180 degrees phase difference, i.e., is an inverted pulse.

The first RF echo signal can be stored and applied to two down-converters. The first down-converter can be centered at the fundamental frequency. The second down-converter can be centered at a harmonic frequency. The two down-converter outputs can be filtered and stored.

A second RF echo signal can be obtained by sending the phase inverted pulse, which is added to the first RF echo signal. The RF summation result can be applied to the same down-converters used for the first transmit. In a selection unit, the ratio of the energy in the envelope-detected fundamental of the first received signal to the energy in the envelope-detected fundamental of the RF summation signal is obtained. This ratio can be used to detect bubble destruction, flow motion, non-symmetrical bubble response to compression and rarefaction pulses. In addition, the ratio of the harmonic output of RF summation to the fundamental of the first transmit is obtained and can be used to measure medium non-linearity, 'B/A'. The two ratios can be sent to a decision maker circuit to determine if the signal is a tissue region or a contrast flow region. If the region is a tissue region, the harmonic output of RF summation is selected; if the region is a contrast flow region, the sum of outputs of both fundamental and harmonic from RF summation is used.

Another method of generating 2 receive bands is to apply 2 different bandpass filters to the received signal from a single transmit. Another method is to use phase inversion processing, transmitting 2 or more pulses that differ only in phase and summing the return signals in various ways to enhance or suppress various portions of the return signals.

BRIEF DESCRIPTION OF THE DRAWINGS

A better understanding of the invention is obtained when the following detailed description is considered in conjunction with the following drawings in which:

FIG. 1 is a diagram of contrast agent flow spectra for a phase inversion wideband harmonic scheme;

FIG. 2 is a diagram of tissue spectra for a phase inversion wideband harmonic scheme;

FIG. 3 is a diagram of tissue spectra for a phase inversion scheme according to the present invention;

FIG. 4 is a diagram of contrast agent flow spectra for a phase inversion scheme according to an implementation of the present invention;

FIG. 6 is a graph of spectra of tissue and contrast agent flow from a single transmit signal;

FIG. 7 is a graph of spectra of tissue and contrast agent flow from phase inversion summation;

FIG. 8 is a graph of spectra of tissue and contrast agent flow from a single transmit signal after filtering at the fundamental frequency;

FIG. 9 is a graph of spectra of tissue and contrast agent flow from phase inversion summation after filtering at the fundamental frequency;

FIG. 10 is a graph of spectra of tissue and contrast agent flow from a single transmit signal after filtering at the second harmonic frequency;

FIG. 11 is a graph of spectra of tissue and contrast agent flow from phase inversion summation after filtering at the second harmonic frequency;

FIGS. 12–14 illustrate imaging results according to various techniques; and

DETAILED DESCRIPTION OF THE INVENTION

Figure 5:
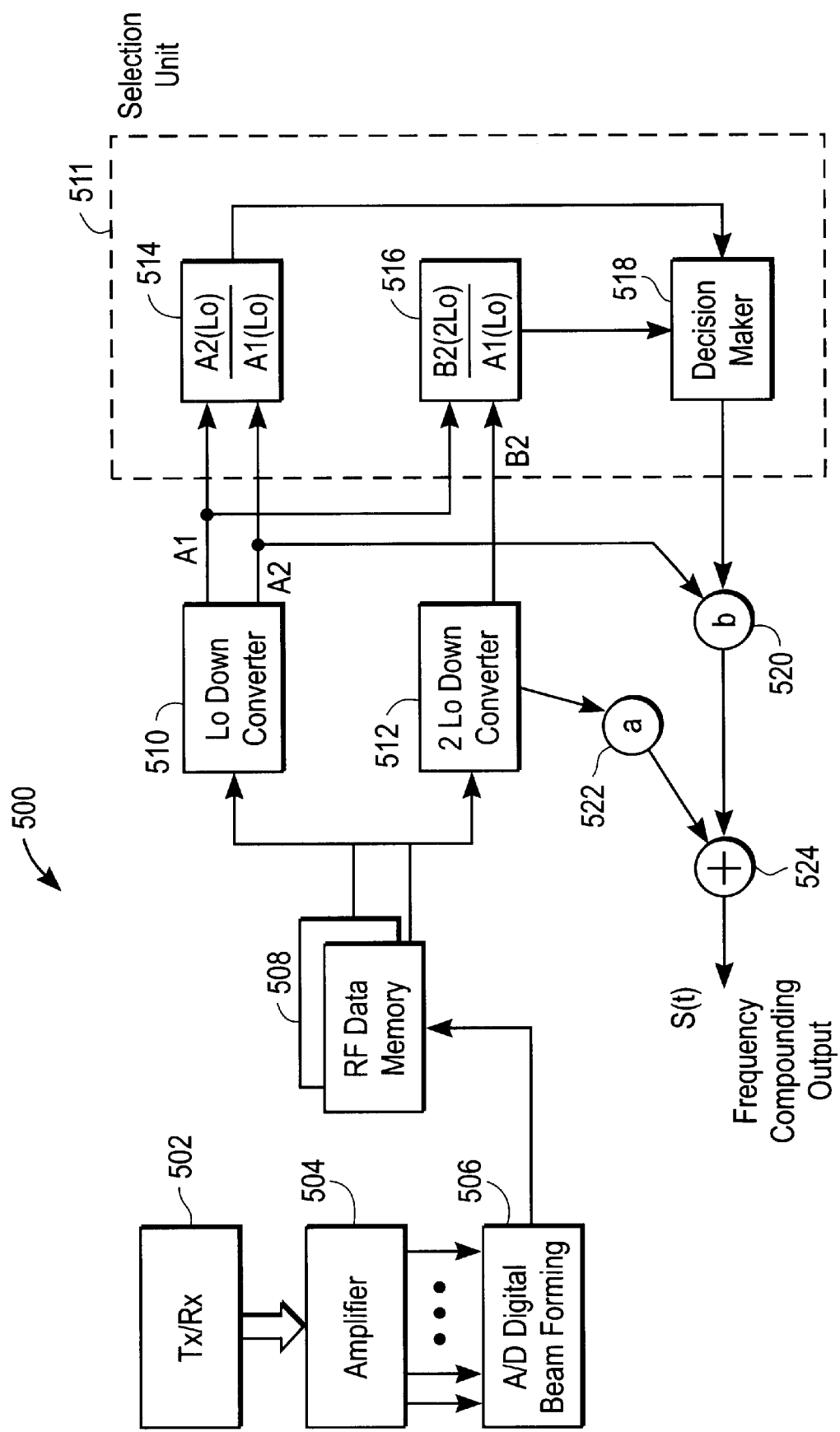
FIG. 5 is a block diagram of an ultrasound system according to an implementation of the present invention.

FIGS. 3–15 illustrate a system and method according to an implementation of the invention. An ultrasound system according to the present invention employs a harmonic imaging filter on tissue only regions and implements frequency compounding filtering for contrast agent flow regions.

Turning now to FIG. 3, a diagram of tissue spectrum according to an implementation of the invention is shown. In particular, the spectrum 301 of the phase inversion summation of tissue regions is shown, filtered by a harmonic filter 302 centered at 4 MHz, where 4 MHz is the first harmonic.

As shown in FIG. 4, frequency compounding is used to filter contrast agent flow. Shown is the spectrum of phase inversion summation for contrast flow regions 303 including a harmonic filter 302 centered at 4 MHz, and a second filter 304 centered at the fundamental frequency (in this case, 2 MHz).

FIG. 5 illustrates an exemplary ultrasound imaging system for implementing the adaptive frequency compounding according to the present invention. The ultrasound imaging system 500 includes a transmit/receive switch 502 for transmitting and receiving ultrasound signals. The signals are provided to an amplifier 504 and then an analog-to-digital digital beamforming unit 506. The data are buffered in an RF data memory 508 and then provided to a pair of down converters 510, 512. The center frequency of the down converter 510 is set at Lo, where Lo is the transmitting frequency. The center frequency of the downconverter 512 is set at 2 Lo.

At the output of the downconverters 510, 512 is a selection unit 511. The selection unit 511 includes a divider 514 at the output of the down converter 510 and a divider 516 at the output of the downconverter 512, which also receives an output from the downconverter 510, as will be explained in greater detail below. The outputs of the divider 514, 526 are provided to a decision maker 518. The decision maker 518 determines from the outputs of the dividers whether the signals are from a tissue region or from a contrast agent flow region, as will be explained in greater detail below.

The decision maker 518 controls the input to a summer circuit 524. If the decision maker determines that the contrast flow regions are being scanned, then the outputs from the downconverters are summed using summer 524. Otherwise, only the output from the first downconverter is output.

If desired, the outputs of the donwconverters may be shaped through application of constant factors a 520 and b 522. As will be explained in greater detail below, in one implementation, the factor a is a constant greater than zero (0); the factor b is a constant less than one (1).

In operation, the system transmits a first pulse which is digitized and sent to both filter-downconverters 510. The filter-downconverter 510 is set at the fundamental frequency Lo. The filter-downconverter 512 is set at the harmonic frequency 2 Lo. In one implementation, the fundamental frequency is 2 MHz and the filters have 60% bandwidth. For example, when transmitting is set at 2 MHz, the Lo of the first downconverter 510 is set at 2 MHz with a bandwidth of 1.2 MHz to cover the fundamental signals from 1.4 MHz to 2.6 MHz. The second downconverter 512 is set at 4 MHz, with a bandwidth of 2.4 MHz to cover the second harmonic signals from 2.8 MHz to 5.2 MHz. The input signals and the output signals are stored in memory.

The system then transmits a second pulse with an inverted phase. The echo signal is digitized and added to the previously digitized RF signal. The RF summation is sent to both filter downconverters 510, 512 with the same setting as in the first transmission.

The outputs of the filter downconverters 510, 512 are provided to a selection unit 511. The selection unit 511 includes a divider 514 and a divider 516. The divider 514 calculates the ratio of the two intensity outputs A1, A2, (e.g., A2/A1) where A1 is the fundamental intensity of the echo from the first transmit, and A2 is the intensity of phase inversion fundamental residue signal (i.e., the sum of the first and second pulses). The divider 516 calculates the ratio of the intensity output B2 and A1 (e.g., B2/A1), where A1 is as before, and B2 is the second harmonic from the phase inversion summation. The outputs of the dividers 514, 516 are applied to a decision maker 518, which determines whether the signals are from a tissue region or from a contrast agent flow region, as will be explained in greater detail below.

In the implementation illustrated, the output of the decision maker 518 controls whether to select tissue harmonic filter for tissue-only regions or frequency compounding filtering for regions with contrast regions. In particular, the decision maker 518 either selects or suppresses the b factor 520 such that the output appears as follows: S(t)=aB2(t) for tissue regions, and S(t)=aB2(t)+bA2(t) for contrast flow regions. S(t) is the system intensity output, B2(t) is the intensity of the phase inversion second harmonic summation, A2(t) is the intensity of the phase inversion fundamental residuals, and a and b are constants between 0 and 1.

Operation of the selection unit 511 is understood with reference to FIGS. 6–11. More particularly, FIG. 6 illustrates the spectra of echoes from a single transmit. The contrast agent flow spectra is represented by 602 and the tissue spectrum is represented by 604. Similarly, FIG. 7 illustrates the spectra for contrast agent flow 702 and tissue 704 spectra when phase inversion summation is implemented. As can be seen, for tissue regions, substantial cancellation occurs when phase inversion summation is employed (i.e., plot 604 vs. 704). However, the contrast flow spectrum 602, 702 does not appear to show significant suppression when phase inversion is employed. Thus, the change in the fundamental frequency residuals is used to discriminate tissue only regions and regions having contrast agent flow.

This is further seen in FIGS. 8 and 9. FIG. 8 illustrates the plot of FIG. 6 filtered at 2 MHz. FIG. 9 illustrates the plot of FIG. 7 after filtering at 2 MHz. Plot 802 is the fundamental component of the contrast flow, and plot 804 is the fundamental component of the tissue echo for a single transmit. In FIG. 9, plot 902 is the fundamental residual of contrast agent flow and plot 904 is the fundamental residual of tissue echo when phase inversion summation is employed. As can be seen, the contrast agent flow 802, 902 does not show the same degree of suppression as the tissue echo 804, 904.

FIGS. 10 and 11 illustrate similar graphs when the second harmonic (e.g., 4 MHz) is filtered. In particular, FIG. 10 illustrates the second harmonic components of a single transmit for contrast agent flow 1002 and tissue 1004. FIG. 11 illustrates the second harmonic components of phase inversion summation passing a second harmonic filter for contrast agent flow 1102 and tissue 1104. Therefore, the ratio of phase inversion harmonic intensity to fundamental intensity of a single transmit can be used for tissue flow discrimination.

More particularly, in tissue regions, the ratio A2/A1 of first transmit fundamental to phase inversion summation should be about −26 to −30 dB in tissue regions, and about −6 to −18 dB in contrast flow regions. Thus, for example, the decision maker 518 implements a threshold table as a function of depth and transmit power. Depending on where the threshold falls, the decision maker can determine if the signals are from contrast or tissue regions. It is noted that in fast tissue regions, the ratio A2/A1 could be close to or cross the threshold for A2/A1 and therefore the ratio B2/A1 may also be used.

In particular, in tissue regions, the ratio B2/A1 of second harmonic summation to fundamental should be at about −15 to −20 dB; for contrast agent regions, the ratio is about −10 dB. Again, a threshold table can be generated as a function of transmit power and depth. If the ratio is determined to cross the threshold, a contrast region is identified.

FIGS. 12–14 illustrate processed signals. In particular, FIG. 12 illustrate the imaged output after adaptive frequency compounding according to the present invention, FIG. 13 illustrates the result if the second harmonic is filtered and FIG. 14 illustrates the result if a wideband harmonic imaging is used. As can be seen, the present invention (FIG. 12) provides a sharper image. It is noted, however, that even if frequency compounding is not used, the present invention provides benefits in determining whether a region is a tissue region or a contrast agent region.

Figure 15:
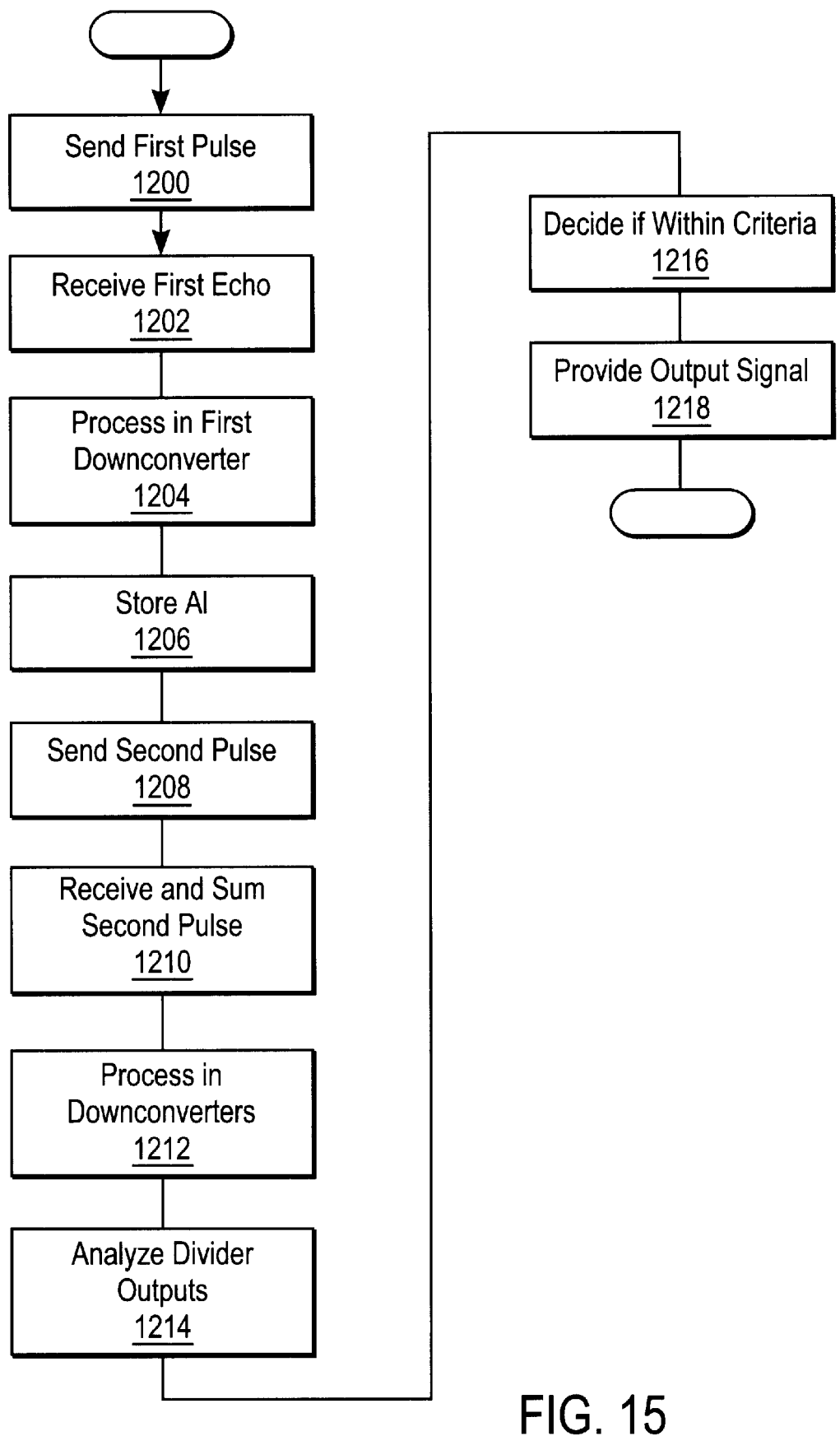
FIG. 15 is a flowchart illustrating operation of an implementation of the invention.

Turning now to FIG. 15, a flowchart illustrating operation of an implementation of the invention is shown. In a step 1200, a first transmit pulse is sent into a body. In a step 1202, the receive echo signal is received. In a step 1204, the echo signal is processed in the first downconverter and stored in a step 1206. As discussed above, the first downconverter includes a filter at the fundamental frequency Lo. The result A1 (Lo), is stored. Next, in step 1208, the second pulse is sent, the pulse having an inverted phase from the first pulse. In step 1210, the echo data from the second pulse are received and summed with the first echo signals. In step 1212, the summed echo data are fed to the first and second downconverters. As discussed above, the second downconverter includes a filter at the second harmonic frequency, 2Lo. The outputs A2(Lo) and B2(2Lo), along with the previously stored A1(Lo), are processed by the selection unit 511. In step 1214, the data are processed by the dividers 514, 516. The resulting ratio outputs (e.g., A2/A1 and B2/A1) are processed by the decision maker 518, in a step 1216, to determine if they fall within the criteria for contrast agent or tissue regions. As discussed above, this includes checking one or more threshold tables (not shown) to determine where the ratios fall. Finally, in a step 1218, the decision maker 518 provides the appropriate output signal to activate or deactivate the factor b 520. The result is a frequency compounding output for contrast agent flow regions.

It is noted that a similar procedure employing contrast sub-harmonic imaging may be employed, as well. For example, when transmitting at 4.0 Mhz, the first downconverter's Lo may be set to 4 MHz, and the second's set to 2 MHz. Then the fundamental signal and the phase inversion fundamental residual are the outputs of the 4 MHz downconverter and the phase inversion signal from the second downconverter is the sub-harmonic signal. It is known that tissues do not generate sub-harmonic signals, but contrast flow bubbles do. The ratio of phase inversion sub-harmonic intensity to fundamental intensity can be used as an input to the decision maker to decide if the fundamental signal is to be used for contrast agent enhancement. At tissue only regions, only the fundamental residual signals will be used for imaging. In contrast flow regions, frequency compounding of fundamental residuals and subharmonic signals can be done to enhance contrast flow.

The invention described in the above detailed description is not intended to be limited to the specific form set forth herein, but on the contrary, it is intended to cover such alternatives, modifications and equivalents as can reasonably be included within the spirit and scope of the appended claims.

What is claimed is:

1. An ultrasound system, comprising:
   transmit and receive circuitry for transmitting and receiving ultrasound signals, the receive circuitry including at least one frequency band selection circuit adapted to:
   select signals disposed within a first frequency band, and
   select signals within a second frequency band, the second frequency band different from the first frequency band; and
   a selection unit adapted to:
   determine if said ultrasound signals are from tissue regions or contrast agent regions; and
   issue a control signal to implement different processing corresponding to one of a tissue region determination and a contrast agent region determination, the control signal operable to select between at least two possible output signals as a function of the determination.

2. An ultrasound system in accordance with claim 1, wherein said ultrasound signals include first echo signals and second echo signals having a different phase than said first echo signals.

3. An ultrasound system in accordance with claim 2, wherein said selection unit includes a first divider adapted to obtain a ratio of first echo signal outputs and second echo signal summation outputs of said at least one frequency band selection circuit.

4. An ultrasound system in accordance with claim 3, wherein said selection unit includes a second divider adapted to obtain a ratio of second echo summation signals and said first echo signal outputs of said at least one frequency band selection circuit.

5. An ultrasound system in accordance with claim 4, wherein said selection unit includes a decision maker adapted to provide said control signal if outputs of said first and second divider meet predetermined criteria.

6. An ultrasound system in accordance with claim 1, further comprising circuitry adapted to:
   in tissue regions perform at least one of: harmonic image processing; echo processing, and grayscale display; and
   in contrast agent regions perform at least one of: frequency compounding, power mode processing, and color display.

7. An image processing system comprising:
   a first frequency band selection circuit adapted to process signals having approximately a first frequency;
   a second frequency band selection circuit adapted to process signals at approximately a second frequency different than said first frequency; and
   a selection unit adapted to:
   determine if signals received into said first frequency band selection circuit and said second frequency band selection circuit are representative of one of tissue regions and contrast agent regions; and
   issue a control signal to implement at least one display processing depending on whether said signals are determined to be representative of said tissue regions or said contrast regions.

8. An image processing system in accordance with claim 7, wherein said second frequency band selection circuit comprises a harmonic filter.

9. An image processing system in accordance with claim 7, wherein said second frequency band selection circuit comprises a sub-harmonic filter.

10. An image processing system in accordance with claim 7, wherein said signals include first echo signals, and second echo signals having a different phase than said first echo signals.

11. An image processing system in accordance with claim 10, wherein said selection unit included a first divider adapted to obtain a ratio of first echo signal outputs of said first frequency band selection circuit and second echo signal summation outputs of said first frequency band selection circuit.

12. An image processing system in accordance with claim 11, wherein said selection unit includes a second divider adapted to obtain a ratio of a second frequency band selection circuit output of second echo summation signals and said first echo signal outputs of said first frequency band selection circuit.

13. An image processing system in accordance with claim 12, wherein said selection unit includes a decision maker adapted to provide said control signal if outputs of said first divider and said second divider meet predetermined criteria.

14. An image processing system in accordance with claim 7, wherein said display processing comprises at least one of frequency compounding, harmonic image processing, echo processing, power mode, gray scale, and color display.

15. A method for determining if ultrasound data are from contrast region or a tissue region, comprising:
   receiving at least one echo signal responsive to at least one pulse;
   responsive to said receiving, comparing at least one parameter derived from a first frequency band with at least one parameter derived from a second frequency band, the second frequency band different than a fundamental frequency band;
   determining whether the at least one echo signal is associated with the contrast region; and
   selecting between at least two possible output signals as a function of the determination.

16. A method in accordance with claim 15, wherein said comparing includes:
   obtaining a ratio of a first output of a first echo signal from said first frequency band;
   obtaining a second output of a second echo signal from said second frequency band; and
   obtaining a ratio of a third output of said second frequency band and said first output.

17. A method according to claim 15, wherein said second frequency band comprises a harmonic frequency band.

18. A method according to claim 15, wherein said second frequency band comprises a subharmonic frequency band.

19. A method according to claim 15, wherein said at least one pulse comprises a first pulse and a second pulse, and the first pulse and the second pulse are phase inverted.

20. A method according to claim 15, wherein:
   said first frequency band comprises a fundamental frequency band; and
   said second frequency band comprises one of a harmonic frequency band and a subharmonic frequency band.

21. A system for determining if ultrasound data are from a contrast region or a tissue region, comprising:
- means for receiving first echo signals responsive to a first pulse;
- means for receiving second echo signals responsive to a second pulse; and
- means for comparing outputs of a fundamental frequency filter and a fundamental harmonic filter responsive to said receiving first echo signals and receiving said second echo signals, the means for comparing including means for obtaining at least two rations from the first and second echo signals.

22. A system in accordance with claim 21, wherein said comparing means includes means for obtaining a ratio of a first output of said first echo signal from said fundamental frequency filter and a second output of said second echo signal from said fundamental frequency filter and means for obtaining a ratio of a third output of said fundamental harmonic filter and said first output.

* * * * *